United States Patent [19]

Dong et al.

[11] Patent Number: 4,927,973
[45] Date of Patent: May 22, 1990

[54] PROCESS FOR CONTINUOUS PURIFICATION OF BISPHENOLS

[75] Inventors: Walter Dong, Gold River, Calif.; Paul V. Shaw; James L. Buechele, both of Houston, Tex.

[73] Assignee: Shell Oil Company, Houston, Tex.

[21] Appl. No.: 285,254

[22] Filed: Dec. 16, 1988

[51] Int. Cl.$^5$ .................. C07C 37/84; C07C 37/68
[52] U.S. Cl. ................................ 568/724; 568/729; 568/749
[58] Field of Search ............... 568/724, 729, 722, 749

[56] References Cited

U.S. PATENT DOCUMENTS

| | | | |
|---|---|---|---|
| 3,326,986 | 6/1967 | Dugan et al. | 260/619 |
| 4,408,087 | 10/1988 | Li | 568/724 |
| 4,529,823 | 7/1985 | Mendiratta | 568/724 |

FOREIGN PATENT DOCUMENTS 1580676  7/1969  France ................. 568/724

Primary Examiner—Werren B. Lone

[57] ABSTRACT

A process for the continuous purification of crude bisphenol which comprises (1) forming a single liquid phase comprising a hot mixture of crude bisphenol and water in a ratio substantially of from about 75% to about 85% weight of crude bisphenol to about 15% to about 25% weight water; (2) continuously feeding this mixture together with a stream of warm water to a first crystallization zone at a temperature sufficient to maintain a bisphenol-rich liquid phase, a water-rich phase and a crystalline phase comprising about 70% to about 95% of the total bisphenol in the mixture; (3) passing the three-phase mixture of bisphenol and water to a second crystallization zone operated at about 85° C. to about 97° C. until about 90% to about 99% of the total bisphenol is crystallized; and (4) recovering the purified bisphenol crystals.

5 Claims, 1 Drawing Sheet

PROCESS FOR CONTINUOUS PURIFICATION OF BISPHENOLS

BACKGROUND OF THE INVENTION

1. Field of the Invention

The present invention relates to a process for the continuous purification of bisphenols. State of the Art The purification of bisphenols from aqueous mixtures thereof is known. In U.S. Pat. No. 3,326,986, a bisphenol product is batch crystallized by a two-phase process in which bisphenol is cooled to below 55° C., a mixture of the desired bisphenol and water is formed and is heated to melt any crystals, agitated, and cooled to a temperature at which a substantial portion of the bisphenol crystallizes.

However, this process is not useful for continuous crystallization and does not lead to high purity crystals of bisphenols which are large and firm so that they are easier to wash and otherwise work up because they do not break in handling.

SUMMARY OF THE INVENTION

The present invention is directed to a process for the continuous purification of crude bisphenol which comprises (1) forming a single liquid phase comprising a hot mixture of crude bisphenol and water in a ratio of from about 75% to about 85% weight of crude bisphenol to about 15% to about 25% weight water; (2) continuously feeding this mixture together with a stream of warm water to a first crystallization zone at a temperature of the combined streams sufficient to maintain a bisphenol-rich phase, a water-rich phase and a crystalline phase comprising about 70% to about 95% of the total bisphenol in the mixture; (3) passing the three-phase mixture of bisphenol and water to one or more crystallization zones operated at about 85° C. to 97° C. until about 90% to about 99% of the total bisphenol is crystallized; and (4) recovering the purified bisphenol crystals.

The above process is useful for the continuous crystallization of bisphenols having large and firm crystals. The crystals formed using the process of the invention form at a much lower temperature than in conventional melt crystallization, the density difference of crystals is high with the water-rich system, so settling is rapid a compared to bisphenol solid-bisphenol melt systems.

The temperature of the hot mixture of step (1) is usually above about 95° C. and preferably above about 105° C. depending on the composition of the mixture. The temperature in step (2) at which the three phases coexist will depend on the composition of the particular mixture, including the particular crude bisphenol, water and impurities. By way of example, the temperature in step (b), when the mixture comprises about 15-20% weight bisphenol and about 80-85% weight water, is about 99° C. to about 101° C. The temperature in step (3) also varies with the composition of the three-phase mixture and the degree of bisphenol feed to be crystallized but is between about 85° C. to about 97° C.

The pressure is adjusted by standard means to maintain the three phases at a particular temperature. Water in the system is kept from flashing to cool the system and causing undesired crystallization by adjusting the pressure. Usually, the pressure is from about atmospheric to about 5 to about 10 psig or higher.

The composition of the mixture to step (1) is from about 75% to about 85% weight crude bisphenol containing undesired by-products, including the isomers and high condensation products from the preparation of bisphenol, and from about 15-25% weight water. Preferably, the mixture comprises about 80% weight crude bisphenol and about 20% water. The amount of impurities present in the crude bisphenol is not critical as long as the solubility of these impurities in the water is not exceeded.

One of skill in the art can readily adjust the rate of mixing and residence time to achieve the desired crystal product.

The crystals of the bisphenol are recovered by conventional techniques known in the art as by filtration, e.g., on an open Buchner funnel lined with a polyester felt or by centrifugation, or the like. Further purification can be accomplished by the same process of the present invention or another conventional crystallization method.

The mother liquor obtained after recover of the bisphenol crystals can be treated to recover residual bisphenol and impurities for recycle to a adduct crystallization system before the water is recycled. Some of the impurities form solid solutions or the like with the bisphenol; therefore, these impurities cannot be completely removed in one crystallization step. To closer approach the purification afforded by batch crystallization of solid solutions in continuous operation additional multiple stages can be used. As an example, in a three-stage continuous crystallizer, the first two stages will operate in the three-phase region. As in the two-stage crystallizer, optimum purification is obtained when the same fraction of solute fed to each stage is crystallized, and the last stage is operated essentially at the same temperature as the last stage of the two-stage case.

The use of water having an acidic nature can aid in the obtaining of bisphenol product reduced in the presence of color as determined by having a reading of about 20 or less in an A.H.P.A. alcoholic solution color test. Usually, it is desirable to use water having a pH of from about 1 to about 6. Numerous conventional mineral and organic acids can be used to adjust the pH, such as hydrohalogenic acids, sulfuric acid, phosphoric acid, acetic, citric, oxalic acids and the like.

Melt systems and solidification of bisphenol alternatively can be combined to improve purity of bisphenol since solid solutions are possible. Injection of steam or cold water can be used to control the temperature and effect phase changes while avoiding the use of heat transfer surfaces.

The simplest practical system then consists of two stages where most of the crystals are formed in the first stage from the three-phase region. The second stage serves to crystallize the remaining BPA. Requirement for product purity dictates the overall recovery, which can be controlled by setting the temperature in stage two and the slurry concentration. The first-stage crystallizer operates essentially isothermally, so temperature cannot be used for control of fractional recovery. Instead, a heat balance must be used, and this can be achieved by controlling the temperature of the feed water.

For a staged system with a solid solution the optimum purity is obtained when the same fraction of solute fed to each stage is crystallized. For example, for a 99% overall recovery in a two-stage system, 90% of the crystals should be formed in stage one and 90% of the remaining 10% solute should be crystallized in the second.

For a two-component system of, e.g., BPA and water, at one particular temperature, about 101° C., two liquids and crystalline BPA coexist in equilibrium. As heat is removed, BPA crystallizes at a constant temperature from the BPA-rich phase along with the generation of additional water-rich phase. When the BPA-rich layer is consumed, further removal of heat results in a temperature drop and the crystallization of a relatively small amount of additional BPA from the aqueous layer. Large, well-formed individual crystals are formed in this mode of operation and purification is improved.

The function of the crystallization process of the present invention is to separate pp-BPA from the reaction by-products. The presence of impurities lowers the three-phase temperature and causes it to fall further in the course of a batch crystallization as the purity of the dissolved BPA decreases. Some of the major impurities include op-BPA and higher condensation products, such as trimers and the like.

Purification involve dissolving the impurities in the water. Solubility in water of the two principle by-products, op-BPA and trimer, is each about 2-4 times that of pp-BPA, but the solution capacity for the impurities is still limited. Once saturated, these impurities will cocrystallize. Accordingly, the solubility of the impurities in the mother liquor should not be exceeded and, thus, the crystallization process of the invention from water starts with a rather pure feed.

The present invention is useful for the purification of bisphenols prepared by conventional procedures used to prepare bisphenols, e.g., from a ketone and a phenol in the presence of an acid or acidic-acting material, including inorganic and organic materials in liquid or solid form. The bisphenols include those prepared by the reaction of a ketone, such as acetone, ethyl methyl ketone, isobutyl methyl ketone, actophenone, cyclohexanone, 1,3-dichloroacetone, and the like with a phenol, such as phenol, o-cresol, m-cresol o-chlorophenol, m-chlorophenol, o-t-butylphenol, 2,5-xylenol, 2,5-di-t-butylphenol, o-phenylphenol and the like. The above is no meant to limit the invention but to illustrate representative examples of ketones and phenols which are known in the art to make desirable bisphenols and for which those of skill in the art can readily substitute other conventional bisphenol reactants.

A typical feed stream to the crystallization process of the invention is a product from the conventional condensation of a carbonyl compound, such as acetone, with phenol to form bisphenol A (BPA) and usually contains from about 25% to about 60% weight of bisphenol A, preferably 15-25% weight, and the remainder unreacted acetone or phenol and undesirable by-products of the reaction, including undesired isomers of the desired product bisphenol A, higher condensation products, water and the like. Usually, the bisphenol A product is distilled to remove acetone, water and excess phenol so that the feed stream contains about 35% bisphenol A and about 65% phenol and impurities. The resulting mixture is treated in a conventional adduct crystallization or other suitable process to initially partially purify the bisphenol. After stripping this initially partially purified bisphenol to remove phenol, the bisphenol of improved purity is subjected to the process of the present invention.

DESCRIPTION OF THE DRAWINGS

A schematic process flow diagram of the water crystallization unit is shown in FIG. 1.

DETAILED DESCRIPTION OF THE INVENTION

Figure 1:
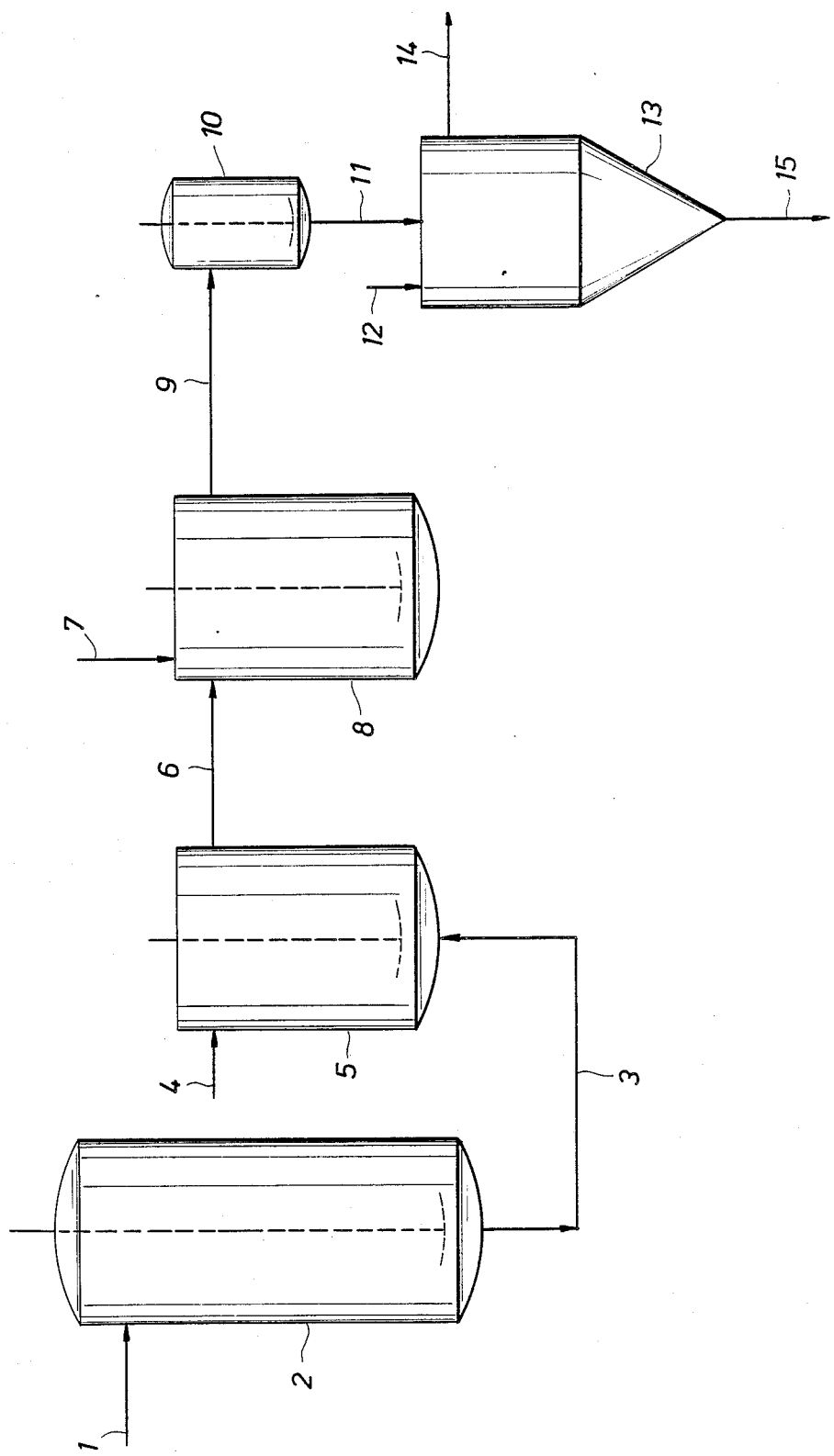

Feed for the unit was made up in feed vessel 2 by charging 100-150 pounds of bisphenol acetone (BPA) and deionized water via line 1 in 80:20 weight ratio, the composition of the BPA-rich phase of the three-phase region. This mixture was heated quiescently under 25-35 psig pressure until it was largely molten, then stirred and heated to about 110° C. The BPA feed system was steam-jacketed or traced throughout, including the injection tip into the bottom of the first-stage crystallizer, line 3. Temperature-controlled, deionized water was fed via line 4 to the top of the first crystallizer stage and was set to control the slurry concentration.

The two crystallizer stages one and two, vessels 5 and 8, respectively, each consisted of a 6-inch diameter by 10.5-inch long, 4.5-liter industrial glass pipe with a rounded bottom equipped with a stirring or agitating means, e.g., four ½-inch baffles and two 2.4-inch slant-blade turbines located 1.5 and 7.5 inches from the bottom, for mixers. Each entire vessel was steam traced and insulated. The product overflowed from 5 into 8 via a heated ½-inch tubing (line 6) from the top of stage one to the top of stage two. To assure the transfer of a representative slurry, timed pulses of nitrogen were injected into stage one so that the flow was in bursts. Otherwise the crystals tended to settle back into the feed stage.

The fraction of BPA crystallized in stage one was controlled by heat balance by varying the temperature of the feed water. The first-stage temperature of about 100° C. was measured to 0.1° C. and used as a reference for setting and re-adjusting the feed water temperature. Cold water was injected into stage two via line 7 for temperature control. A pressure of about 5-10 psig was maintained on the system to assure that the BPA feed would not flash cool and precipitate solids.

At start-up, crystallizer stage one was filled and stage two was partially filled with 95° C. water, low enough to induce rapid crystallization. At the normal operating temperature of about 100° C., crystallization is hard to initiate because the liquid feed can persist for a long time at a slightly subcooled state. A small amount of BPA feed wa added and allowed to disperse and solidify to form agglomerates of poor quality. The water temperature was raised to about 99.5° C. and the flow of water and BPA was restarted. The first crystallizer contents were visually inspected to assure the presence of three phases as evidenced by the globules of crystals wetted with the BPA-rich phase.

Stage two was operated at 85° C. to 97° C., low enough to assure the absence of the BPA-rich layer yet high enough to keep the impurities in solution.

The slurry from stage two overflowed via line 9 into a temperature-controlled surge vessel 10 from which batches of crystals were passed via line 11, filtered and washed with hot water injected via line 12 in a Buchner funnel 13 lined with a polyester felt. The wet cake was removed via line 15 and mother liquor was recovered via line 14. and optionally recycled after conventional clean-up.

Results of experiments conducted as described above are set forth in Table 1.

TABLE 1
Effect of Crystallization Temperature and Number of Phases

| Run | Two-Phase | | | | Three-Phase | | |
|---|---|---|---|---|---|---|---|
| | 1 | 2 | 3 | 4 | 5 | 6 | 7 |
| Stage 1 Temp, °C. | 97 | 97.2 | 98 | 98.7 | 99.3 | 99.5 | 99.3 |
| Res Time, hr | 0.5 | 0.5 | 0.5 | 0.5 | 0.5 | 0.5 | 0.5 |
| Filtration T, °C. | 95 | 95 | 95 | 85 | 85 | 95 | 95 |
| Slurry Concentration, % w | 10.7 | 10.7 | 10.7 | 10.2 | 10.2 | 10.2 | 10.2 |
| Wash/Feed | 0.14 | 0.14 | 0.14 | 0.14 | 0.14 | 0.14 | 0.14 |
| Wash H$_2$O T, °C.[b] | 95 | 96 | 97 | 100 | 99 | 95 | 95 |
| Times Washed | 1 | 1 | 1 | 1 | 1 | 1 | 1 |
| Solids in ML, % w | | 0.527 | | | | 0.582 | 0.582 |
| BPA Recovery, % | | 94.5 | | | | 93.4 | 94.1 |
| Crystal Habit | | (a) | (a) | (a) | (a) | (c) | (c) | (c) |
| Total Impurities, Less Phenol, ppm | 1701 | 497 | 425 | 417 | 332 | 330 | 327 | 326 |

[a]Fine-grain agglomerates.
[b]Actual wash temperature was probably slightly lower.
[c]Single crystals and coarse agglomerates.
[d]Assumed all crystals formed in first stage.

Results of these experiments illustrate that when the crystallization is conducted continuously at a temperature in which three phases (runs 5–7) coexist, the product is desirable single crystals and coarse agglomerates which have good storage stability and are purer than the crystals from batch crystallization at a temperature in which only two phases coexist.

While the invention has been illustrated with particular apparatus, those skilled in the art will appreciate that analogous or equivalent apparatus can be used.

What is claimed is:

1. A process for the continuous purification of crude bisphenol which comprises (1) forming a single liquid phase comprising a hot mixture of crude bisphenol and water in a ratio substantially of from about 75% to about 85% weight of crude bisphenol to about 15% to about 25% weight water; (2) continuously feeding this mixture together with a stream of warm water to a first crystallization zone at a temperature of the combined streams sufficient to maintain a bisphenol-rich liquid phase, a water-rich phase and a crystalline phase comprising about 70% to about 95% of the total bisphenol in the mixture; (3) passing the three-phase mixture of bisphenol and water to a second crystallization zone operated at about 85° C. to about 97° C. until about 90% to about 99% of the total bisphenol is crystallized; and (4) recovering the purified bisphenol crystals.

2. The process according to claim 1 wherein the bisphenol is 2,2-bis(4-hydroxyphenyl) propane.

3. The process according to claim 2 wherein the water has a pH of from about 1 to about 6.

4. The process according to claim 1 wherein adduct crystallization is used prior to or subsequent to the process.

5. The process according to claim 1 wherein steam or cold water is injected into a crystallizer to control the temperature.

* * * * *